(12) United States Patent
Graebner

(10) Patent No.: US 9,316,617 B2
(45) Date of Patent: Apr. 19, 2016

(54) APPARATUS AND METHOD FOR EDDY CURRENT INSPECTION OF STRUCTURES

(71) Applicant: The Boeing Company, Chicago, IL (US)

(72) Inventor: Kim E. Graebner, Derby, KS (US)

(73) Assignee: The Boeing Company, Chicago, IL (US)

( * ) Notice: Subject to any disclaimer, the term of this patent is extended or adjusted under 35 U.S.C. 154(b) by 312 days.

(21) Appl. No.: 13/925,804

(22) Filed: Jun. 24, 2013

(65) Prior Publication Data
US 2014/0375309 A1    Dec. 25, 2014

(51) Int. Cl.
*G01N 27/82* (2006.01)
*G01N 27/90* (2006.01)

(52) U.S. Cl.
CPC .............. *G01N 27/90* (2013.01); *G01N 27/902* (2013.01)

(58) Field of Classification Search
CPC .......................... G01N 27/902; G01N 27/9013
USPC ................................................... 324/220, 240
See application file for complete search history.

(56) References Cited

U.S. PATENT DOCUMENTS

| | | | |
|---|---|---|---|
| 5,254,944 A | 10/1993 | Holmes et al. | |
| 6,076,407 A * | 6/2000 | Levesque et al. | ............... 73/623 |
| 6,558,240 B2 | 5/2003 | Negley | |
| 6,670,808 B2 * | 12/2003 | Nath et al. | .................... 324/230 |
| 2004/0217759 A1 | 11/2004 | Burkhardt et al. | |
| 2008/0042646 A1 | 2/2008 | Burkhardt et al. | |

FOREIGN PATENT DOCUMENTS

EP      0502592 A1    9/1992

OTHER PUBLICATIONS

Olympus "Eddy Current Scanners" Brochure, Jan. 1, 2009, XP055147236, Retrieved from the Internet: URL: http://www.olympus-ims.com/data/File/nortec-scanners/Nortec_Scanners.en.pdf, 2 pages (the whole document).
Olympus "Eddy Current Probes and Accessories" Brochure, Jan. 1, 2010, XP055147234, Retrieved from the Internet: URL: http://www.epsilon-ndt.com/images/uploads/1337152816_pdf.pdf, 20 pages (p. 6).

(Continued)

*Primary Examiner* — Reena Aurora

(57) ABSTRACT

There is provided a probe apparatus. The probe apparatus has a first end configured to connect to a rotating scanner device. The probe apparatus further has a second end with two or more eddy current elements. The second end further has a positioning mechanism configured to position the two or more eddy current elements against cavity walls of an annular cavity of a structure to be inspected with the probe apparatus, when the probe apparatus is positioned within the annular cavity. The second end further has an aligning mechanism coupled to the positioning mechanism. The aligning mechanism is configured to align the two or more eddy current elements in a perpendicular position with respect to the cavity walls of the annular cavity, when the probe apparatus is positioned within the annular cavity.

20 Claims, 12 Drawing Sheets

(56) References Cited

OTHER PUBLICATIONS

European Patent Office Extended European Search Report for Counterpart Patent Application No. EP14172178.7-1554, Applicant The Boeing Company, dated Oct. 23, 2014, 6 pages.

Olympus NDT Inc. Eddy Current Rotating Scanners and Eddy Current Probes product information web pages from <www.olympus-ims.com>, 2009, 3 pages.

* cited by examiner

APPARATUS AND METHOD FOR EDDY CURRENT INSPECTION OF STRUCTURES

BACKGROUND

1) Field of the Disclosure

The disclosure relates generally to devices and methods for non-destructive inspection (NDI) of structures, and more particularly, to devices and methods for eddy current NDI of annular cavities, such as tapered, annular cavities, of structures of air vehicles.

2) Description of Related Art

Non-destructive inspection (NDI) of a structure typically involves inspecting the structure without having to significantly disassemble the structure and without causing harm to the structure. NDI is often used to inspect air vehicle structures, such as aircraft and rotorcraft structures, to detect any internal or external damage to the structures, for example, cracks, crack formations, corrosion, impact damage, or other types of internal or external damage, and to validate the structural health of such structures. In particular, NDI may be useful for inspecting and detecting cracks or crack formations in structures of an aircraft, such as annular cavities or bores of terminal fitting structures that attach aircraft wings to the aircraft.

Known NDI devices and methods exist for inspecting and detecting cracks or crack formations in annular cavities or bores of terminal fitting structures of an aircraft. For example, one such known NDI method of inspection and detection of cracks or crack formations of such annular cavities or bores of terminal fitting structures includes applying a fluorescent penetrant material to the interior of the annular cavity or bore of the terminal fitting structure to be inspected and observing with a black light any fluorescent penetrant material that flows into a crack or crack formation. However, such known method of using a fluorescent penetrant material typically requires that the interior of the annular cavity or bore of the terminal fitting structure be initially manually cleaned to remove any paint, grease, or other surface contaminants. Such manual cleaning of the interior of the annular cavity or bore of the terminal fitting structure to be inspected may prove challenging where the inspection area is difficult to manually access and/or observe. In addition, such known method of using a fluorescent penetrant material typically requires several applications of fluorescent penetrant to the interior of the annular cavity or bore, and several subsequent removals of excess fluorescent penetrant material from the interior of the annular cavity or bore, of the terminal fitting structure to be inspected. Such applications and subsequent removals of excess fluorescent penetrant material may be difficult to visually observe and may result in cracks or crack formations being missed by visual inspection. Moreover, such applications and subsequent removals of excess fluorescent penetrant material may be labor intensive and time consuming to perform, which may, in turn, result in increased costs for conducting such known NDI method.

In addition, a known eddy current NDI method exists for inspecting and detecting cracks or crack formations in annular cavities or bores of terminal fitting structures of an aircraft. Eddy current testing with an eddy current surface probe is based on inducing electron flow (eddy currents) in electrically conductive material. Any defect in the material, such as cracks or other discontinuities, may disrupt the flow of the eddy currents. Higher frequency signals may be used to detect surface or near-surface flaws, and lower frequencies may be used for deeper, subsurface defect detection. Such known eddy current NDI method involves manually holding a single eddy current coil against the interior of the annular cavity or bore of a terminal fitting structure and attempting to maintain a normalcy of the single eddy current coil to the annular cavity or bore, while scanning and indexing a known eddy current surface probe around the annular cavity or bore, and while watching a signal display on or connected to the known eddy current surface probe. However, such manual holding of the single eddy current coil, while scanning and indexing with the eddy current surface probe and watching the signal display, may prove challenging due to difficulty in manually accessing the interior of the annular cavity or bore of the terminal fitting structure to be inspected, and due to difficulty in maintaining the single eddy current coil normal to the interior surface of the cavity or bore of the terminal fitting structure to be inspected. These difficulties may be compounded when such known eddy current NDI method is conducted in large diameter, non-cylindrical, annular cavities or bores, such as tapered, annular cavities or bores, that are to be inspected. Moreover, it may be difficult and/or time-consuming to position and place the single eddy current coil against the tapered, annular cavity or bore of the terminal fitting structure to be inspected, due to the difficulty in manually accessing the often tight area and due to the necessity that the single eddy current coil be in proper alignment against the tapered, annular cavity or bore of the terminal fitting structure to be inspected.

Accordingly, there is a need in the art for an improved NDI apparatus and method for eddy current inspection of structures that provide advantages over known devices and methods.

SUMMARY

This need for an improved NDI apparatus and method for eddy current inspection of structures is satisfied by this disclosure. As discussed in the below detailed description, embodiments of the improved NDI apparatus and method for eddy current inspection of structures may provide significant advantages over existing devices and methods.

In an embodiment of the disclosure, there is provided a probe apparatus. The probe apparatus comprises a first end configured to connect to a rotating scanner device. The probe apparatus further comprises a second end. The second end comprises two or more eddy current elements. The second end further comprises a positioning mechanism configured to position the two or more eddy current elements against cavity walls of an annular cavity of a structure to be inspected with the probe apparatus, when the probe apparatus is positioned within the annular cavity. The second end further comprises an aligning mechanism coupled to the positioning mechanism. The aligning mechanism is configured to align the two or more eddy current elements in a perpendicular position with respect to the cavity walls of the annular cavity, when the probe apparatus is positioned within the annular cavity.

In another embodiment of the disclosure, there is provided a probe apparatus for eddy current inspection of a tapered, annular cavity of a structure of an air vehicle. The probe apparatus comprises a connector end configured to connect to a rotating scanner device. The probe apparatus further comprises a sensor end connected to the connector end via a body portion. The sensor end comprises three foot portions. The sensor end further comprises two eddy current elements comprising a reference eddy current coil attached to one foot portion and a test eddy current coil attached to another foot portion. The sensor end further comprises a positioning mechanism configured to position the two or more eddy current elements against cavity walls of a tapered, annular cavity of a structure of an air vehicle to be inspected with the probe apparatus, when the probe apparatus is positioned within the tapered, annular cavity. The sensor end further comprises an aligning mechanism coupled to the positioning mechanism. The aligning mechanism is configured to align the two or more eddy current elements in a perpendicular position with respect to the cavity walls of the tapered, annular cavity, when the probe apparatus is positioned within the tapered, annular cavity.

In another embodiment of the disclosure, there is provided a differential method of performing an eddy current inspection of an annular cavity of a structure. The method comprises the step of attaching a rotating scanner device to a connector end of a probe apparatus. The probe apparatus comprises a sensor end having two or more eddy current elements, a positioning mechanism, and an aligning mechanism. The method further comprises the step of inserting the probe apparatus into an annular cavity of a structure to be inspected and rotating the probe apparatus with the rotating scanner device. The method further comprises the step of positioning with the positioning mechanism the two or more eddy current elements against cavity walls of the annular cavity to be inspected with the probe apparatus. The method further comprises the step of aligning with the aligning mechanism the two or more eddy current elements, so that each of the two or more eddy current elements is in a perpendicular position with respect to the cavity walls of the annular cavity to be inspected with the probe apparatus. The method further comprises the step of emitting and receiving signals to and from the two or more eddy current elements and the rotating scanner device to obtain data providing an indication of structural health of the structure.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and will fully convey the scope of the disclosure to those skilled in the art.

Figure 1A:
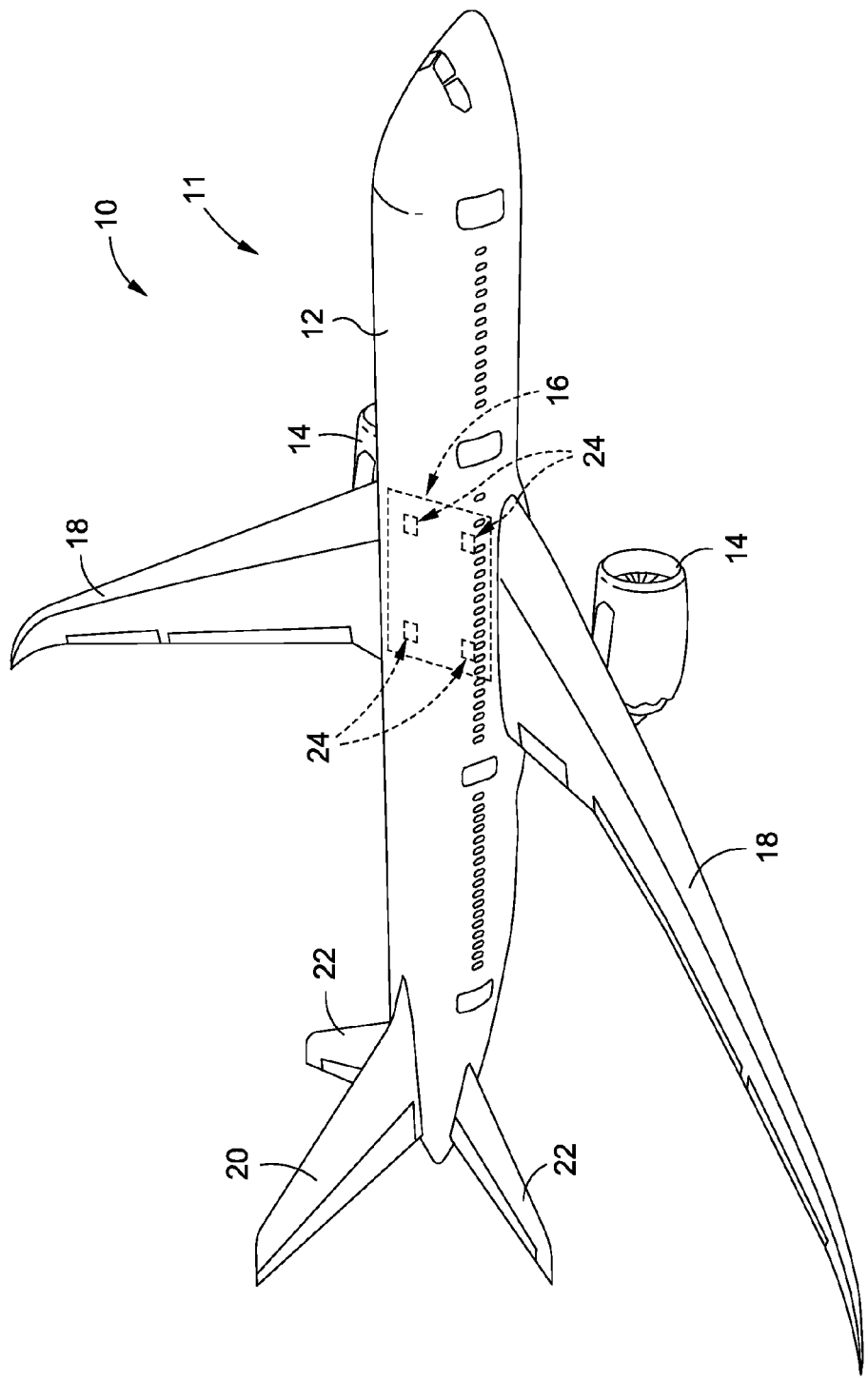
FIG. 1A is an illustration of a perspective view of an air vehicle having one or more structures that may be inspected with embodiments of a probe apparatus and a method of the disclosure.

Now referring to the Figures, FIG. 1A is an illustration of a perspective view of a known air vehicle 10, such as in the form of an aircraft 11, having one or more structures 24 that may be inspected using embodiments of a probe apparatus 70 (see FIGS. 4-8) and a method 150 (see FIG. 9) of the disclosure. As shown in FIG. 1A, the air vehicle 10, such as in the form of aircraft 11, comprises a fuselage 12, one or more propulsion units 14, a wing box 16, wings 18, a tail vertical stabilizer 20, and tail horizontal stabilizers 22. Although the aircraft 11 shown in FIG. 1A is generally representative of a commercial passenger aircraft having one or more structures 24 that may be inspected using embodiments of the probe apparatus 70 (see FIGS. 4-8) and the method 150 (see FIG. 9) disclosed herein, the teachings of the disclosed embodiments of the probe apparatus 70 (see FIGS. 4-8) and the method 150 (see FIG. 9) may be equally applicable to inspection of structures 24 on other air vehicles 10, such as cargo aircraft, military aircraft, rotorcraft such as helicopters, and other suitable types of air vehicles.

Preferably, the inspection of the one or more structures 24 (see FIG. 1A) performed with the probe apparatus 70 (see FIGS. 4-8) and the method 150 (see FIG. 9) is non-destructive inspection (NDI) involving inspection of the one or more structures 24 (see FIG. 1A) without having to significantly disassemble the structures 24 and without causing harm to the structures 24, in order to detect any internal or external damage to the structures 24, for example, cracks or crack formations, and to validate the structural health of the structures 24. Embodiments of the probe apparatus 70 (see FIGS. 4-8) and the method 150 (see FIG. 9) of the disclosure may preferably be used for non-destructive inspection and detection of cracks or crack formations in structures 24 (see FIG. 1B) of an aircraft 11 (see FIG. 1A), such as terminal fittings 26 (see FIG. 1B) of the wing box 16 (see FIG. 1A) that attach wings 18 (see FIG. 1A) to the aircraft 11 (see FIG. 1A), and in particular, in annular cavities 28 (see FIG. 1B) or bores, such as tapered, annular cavities 28a (see FIG. 1B) or bores, of or formed in the terminal fittings 26 (see FIG. 1B).

Figure 1B:
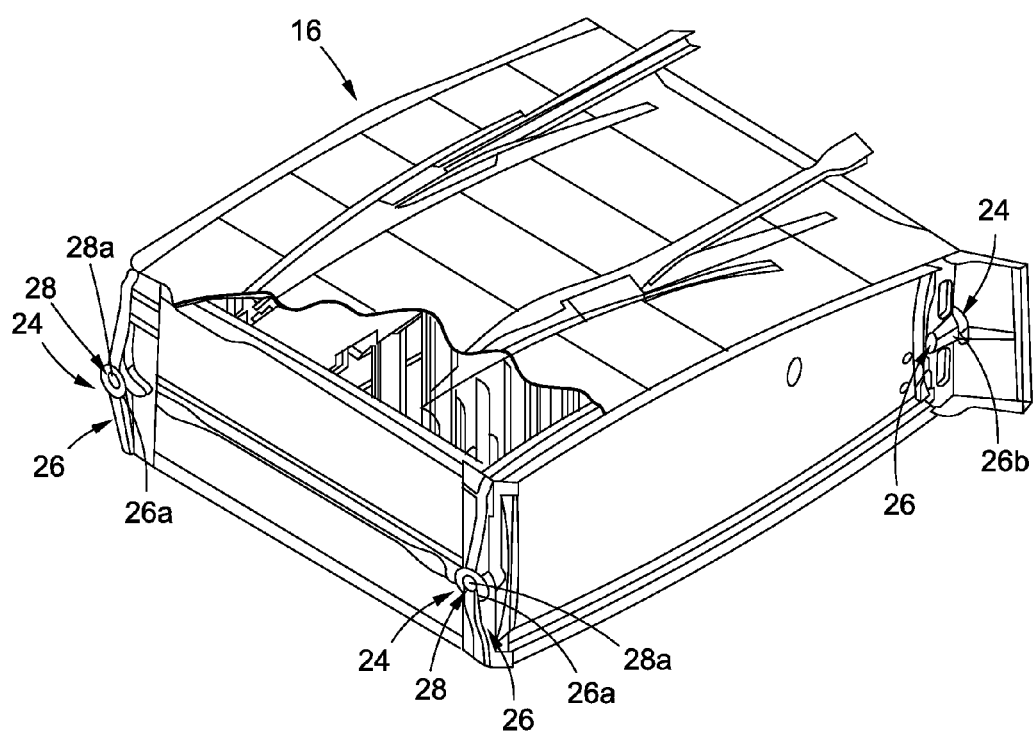
FIG. 1B is an illustration of a close-up, perspective view of a wing box of FIG. 1A having terminal fittings that may be inspected with embodiments of a probe apparatus and a method of the disclosure.

FIG. 1B is an illustration of a close-up, perspective view of the known wing box 16 of FIG. 1A having structures 24, such as terminal fittings 26, that may be inspected with embodiments of the probe apparatus 70 (see FIGS. 4-8) and the method 150 (see FIG. 9) of the disclosure. FIG. 1B shows terminal fittings 26, such as in the form of forward terminal fittings 26a and aft terminal fitting 26b, where each terminal fitting 26 has an annular cavity 28 or bore, such as in the form of a tapered, annular cavity 28a or bore. As discussed in detail below, embodiments of the probe apparatus 70 (see FIGS. 4-8) may be inserted into the annular cavity 28 (see FIG. 1B) or bore, such as in the form of a tapered, annular cavity 28a or bore, to perform non-destructive inspection.

Figure 1C:
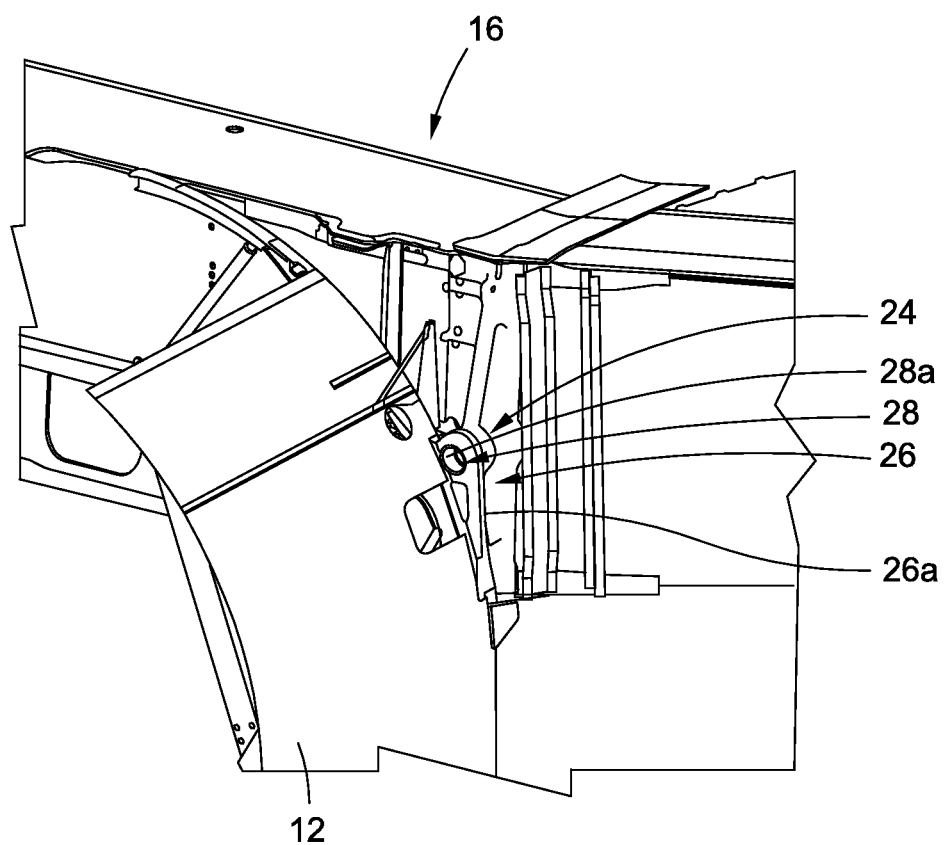
FIG. 1C is an illustration of a close-up, cutaway, perspective view of a terminal fitting of FIG. 1B that may be inspected with embodiments of a probe apparatus and a method of the disclosure.

FIG. 1C is an illustration of a close-up, cutaway, perspective view of the known wing box 16 of FIG. 1B having structure 24, such as terminal fitting 26, in the form of forward terminal fitting 26a, with the annular cavity 28 or bore, such as the tapered, annular cavity 28a or bore, that may be inspected with embodiments of the probe apparatus 70 (see FIGS. 4-8) and the method 150 (see FIG. 9) of the disclosure.

Figure 2:
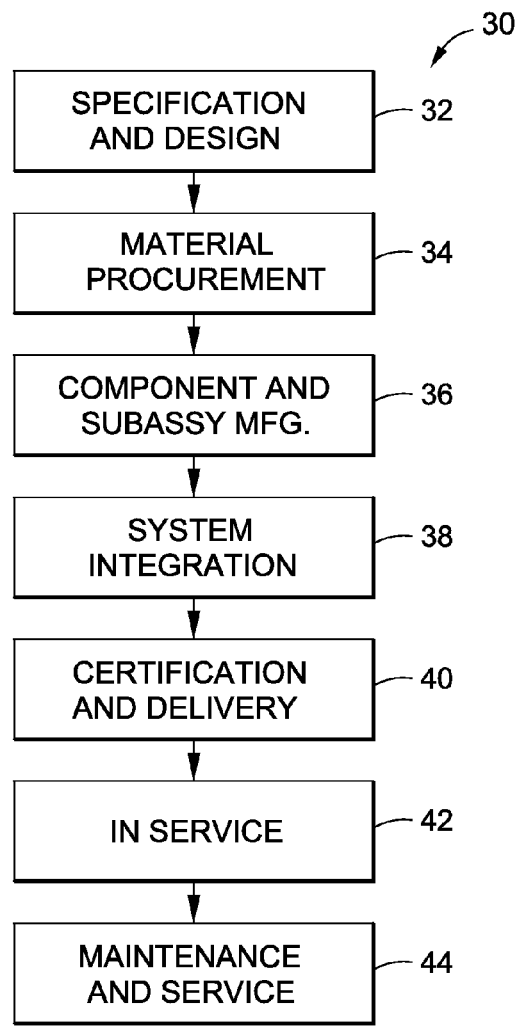
FIG. 2 is an illustration of a flow diagram of an embodiment of an aircraft manufacturing and service method of the disclosure.
Figure 3:
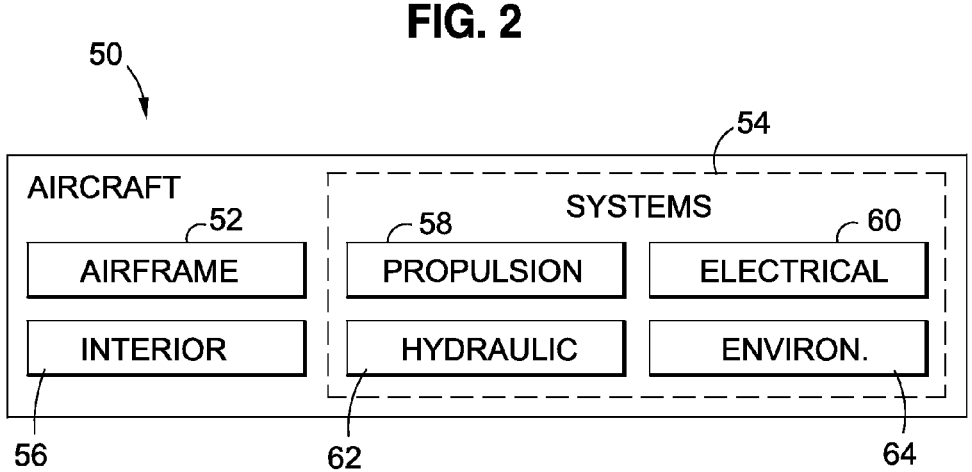
FIG. 3 is an illustration of a functional block diagram of an embodiment of an aircraft of the disclosure.

FIG. 2 is an illustration of a flow diagram of an embodiment of an aircraft manufacturing and service method 30 of the disclosure. FIG. 3 is an illustration of a functional block diagram of an embodiment of an aircraft 50 of the disclosure. Referring to FIGS. 2-3, embodiments of the disclosure may be described in the context of the aircraft manufacturing and service method 30 as shown in FIG. 2 and the aircraft 50 as shown in FIG. 3. During pre-production, exemplary aircraft manufacturing and service method 30 may include specification and design 32 of the aircraft 50 and material procurement 34. During manufacturing, component and subassembly manufacturing 36 and system integration 38 of the aircraft 50 takes place. Thereafter, the aircraft 50 may go through certification and delivery 40 in order to be placed in service 42. While in service 42 by a customer, the aircraft 50 may be scheduled for routine maintenance and service 44 (which may also include modification, reconfiguration, refurbishment, and other suitable services).

Each of the processes of the aircraft manufacturing and service method 30 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may include an airline, leasing company, military entity, service organization, and other suitable operators.

As shown in FIG. 3, the aircraft 50 produced by the exemplary aircraft manufacturing and service method 30 may include an airframe 52 with a plurality of systems 54 and an interior 56. Examples of the plurality of systems 54 may include one or more of a propulsion system 58, an electrical system 60, a hydraulic system 62, and an environmental system 64. Any number of other systems may be included. Although an aerospace example is shown, the principles of the invention may be applied to other industries, such as the automotive industry.

Methods and systems embodied herein may be employed during any one or more of the stages of the aircraft manufacturing and service method 30. For example, components or subassemblies corresponding to component and subassembly manufacturing 36 may be fabricated or manufactured in a manner similar to components or subassemblies produced while the aircraft 50 is in service. Also, one or more apparatus embodiments, method embodiments, or a combination thereof, may be utilized during component and subassembly manufacturing 36 and system integration 38, for example, by substantially expediting assembly of or reducing the cost of the aircraft 50. Similarly, one or more of apparatus embodiments, method embodiments, or a combination thereof, may be utilized while the aircraft 50 is in service, for example and without limitation, to maintenance and service 44.

Figure 4:
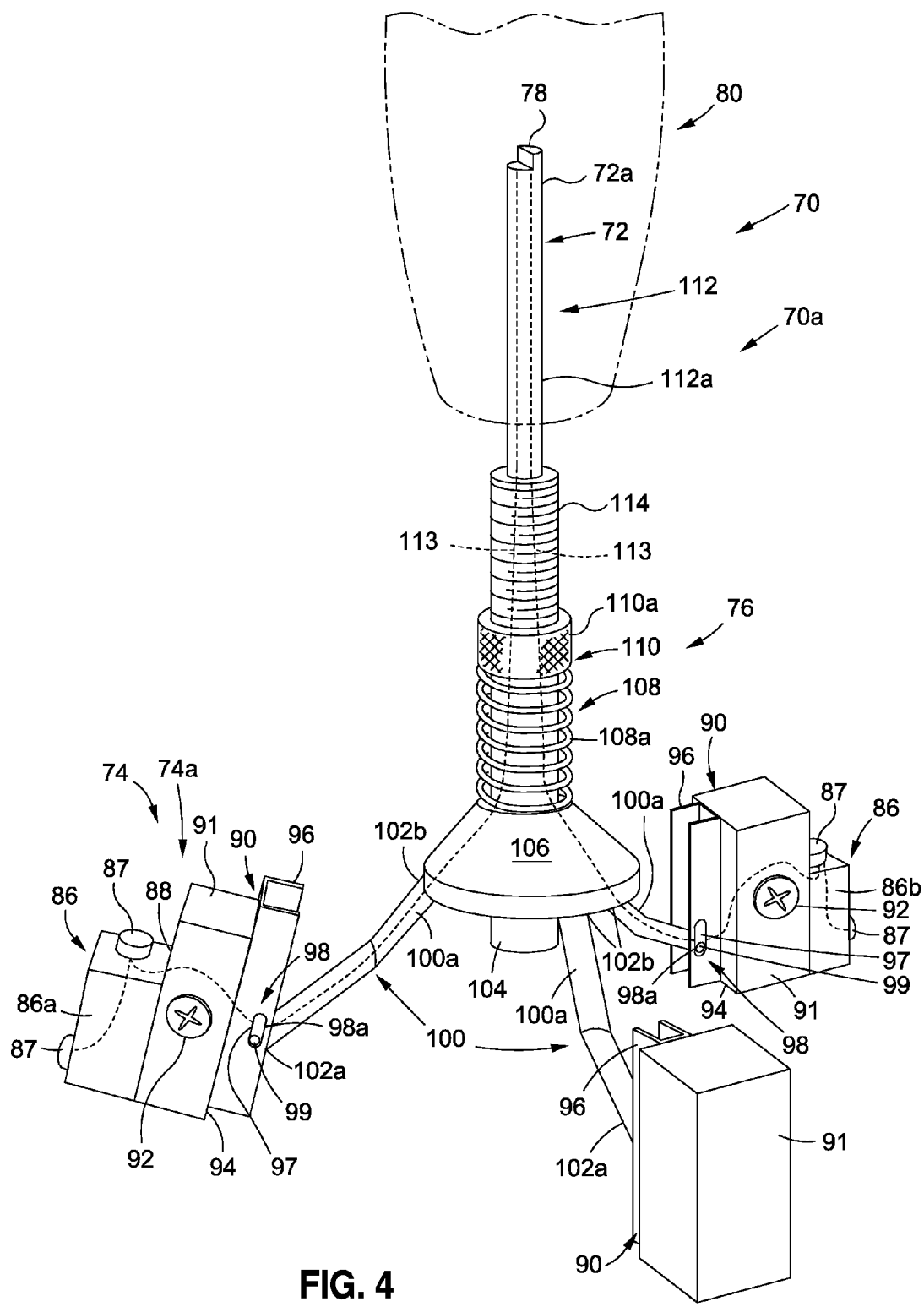
FIG. 4 is an illustration of a side perspective view of an embodiment of a probe apparatus of the disclosure.

In an embodiment of the disclosure, as shown in FIG. 4, there is provided a probe apparatus 70. FIG. 4 is an illustration of a side perspective view of an embodiment of the probe apparatus 70, such as in the form of an eddy current inspection probe apparatus 70a, of the disclosure. As shown in FIG. 4, the probe apparatus 70 comprises a first end 72, a second end 74, and a body portion 76. The first end 72 (see FIG. 4) is preferably configured to connect to a rotating scanner device 80 (see FIG. 4), such as a known eddy current inspection rotating scanner device 80a (see FIG. 5). As further shown in FIG. 4, the first end 72 comprises a connector end 72a having a connector plug 78 configured to connect to the rotating scanner device 80.

The second end 74 (see FIG. 4) comprises a sensor end 74a (see FIG. 4). The second end 74 (see FIG. 4), in the form of sensor end 74a (see FIG. 4), comprises two or more eddy current elements 86 (see FIG. 4). As shown in FIG. 4, the two or more eddy current elements 86 preferably comprise eddy current coils, such as in the form of at least one reference eddy current coil 86a, and at least one test eddy current coil 86b. Each of the two or more eddy current elements 86 preferably comprise two or more electromagnetic coil elements 87 (see FIG. 4). As shown in FIG. 4, the electromagnetic coil elements 87 of the eddy current elements 86 are preferably connected to the rotating scanner device 80 via excitation and signal wiring 113 that runs from each of the electromagnetic coil elements 87, through foot portions 90, along positioning arm elements 100a, through shaft element 112, to the connector end 72a, and to the rotating scanner device 80.

As shown in FIG. 4, the probe apparatus 70 further comprises three or more foot portions 90. Preferably, the probe apparatus 70 has three foot portions 90. However, the probe apparatus 70 may have four foot portions 90 or another suitable number of foot portions 90. As further shown in FIG. 4, each foot portion 90 may comprise a mounting element 91 attached to a base element 96. As further shown in FIG. 4, the mounting element 91 preferably has a first side 88 configured for attachment and mounting of an eddy current element 86 to the mounting element 91 of the foot portion 90, and preferably has a second side 94 configured for attachment and mounting of the base element 96 to the mounting element 91. As further shown in FIG. 4, the mounting element 91 may have one or more attachment elements 92, such as in the form of a bolt or screw, configured to attach the eddy current element 86 to the mounting element 91 of the foot portion 90. As further shown in FIG. 4, each foot portion 90 is preferably coupled to a positioning mechanism 100, and each foot portion 90 is preferably coupled to an aligning mechanism 98.

Figure 8:
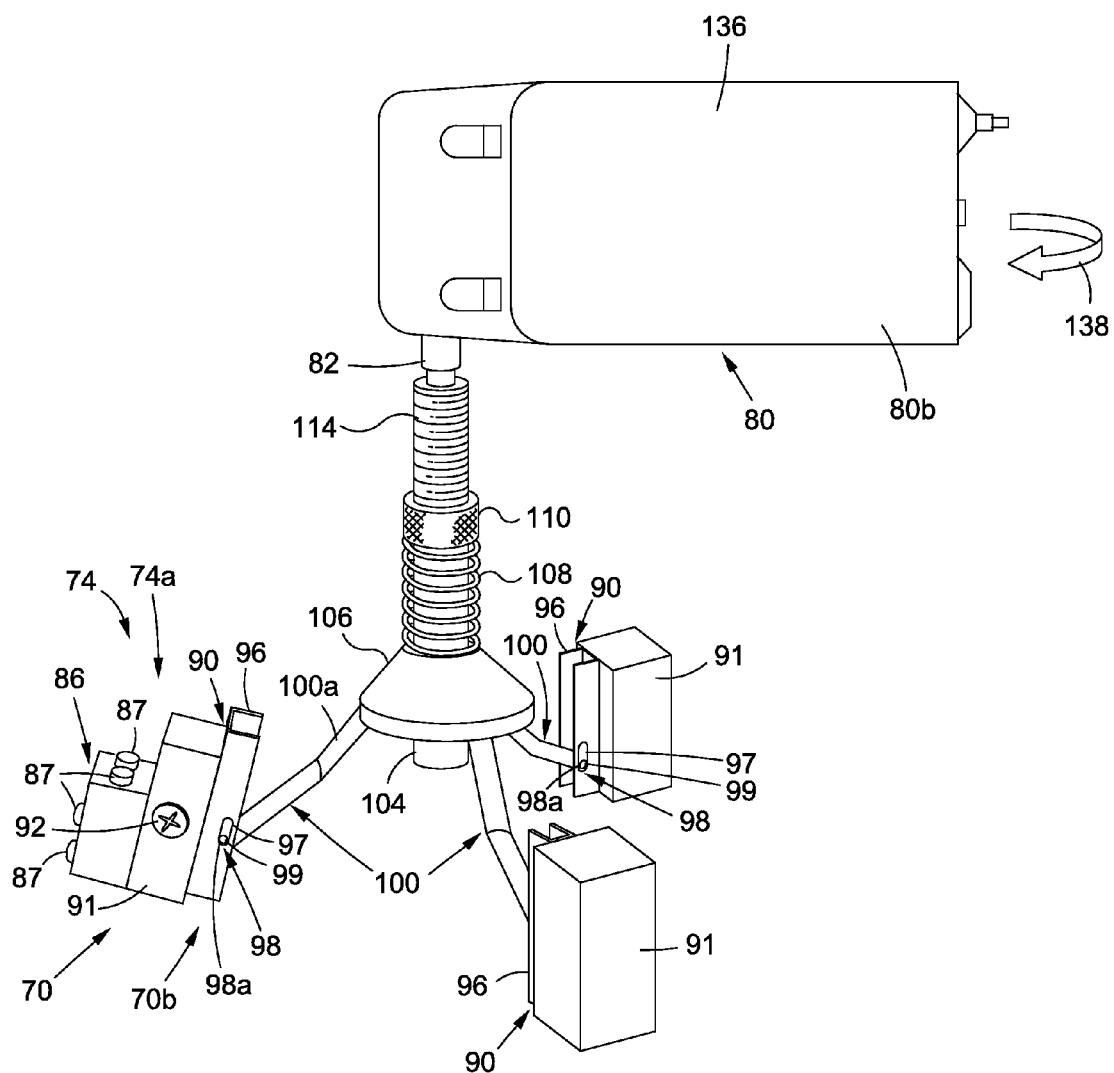
FIG. 8 is an illustration showing rotation of another embodiment of a rotating scanner device attached to another embodiment of a probe apparatus of the disclosure shown in a side perspective view; and, FIG. 9 is a flow diagram illustrating an embodiment of a method of the disclosure.

In one embodiment as shown in FIG. 4, the reference eddy current coil 86a having electromagnetic coil elements 87 is preferably attached to one foot portion 90 of the three or more foot portions 90, and the test eddy current coil 86b having electromagnetic coil elements 87 is preferably attached to another separate foot portion 90 of the three or more foot portions 90. In another embodiment as shown in FIG. 8, the electromagnetic coil elements 87 of both the reference eddy current coil 86a (see FIG. 4) and the test eddy current coil 86b (see FIG. 4) may be attached to one eddy current element 86, and the one eddy current element 86 may be attached to one foot portion 90 of the three or more foot portions 90.

As shown in FIG. 4, the second end 74, such as in the form of sensor end 74a, further comprises the positioning mechanism 100 configured to position the two or more eddy current elements 86 against cavity walls 115 (see FIG. 6B) of an annular cavity 28 (see FIG. 6B) or bore of a structure 24 (see FIG. 1A), such as a terminal fitting 26 (see FIG. 6B) to be inspected with the probe apparatus 70 (see FIG. 4), when the probe apparatus 70 is positioned within the annular cavity 28 (see FIG. 6B) or bore. As further shown in FIG. 4, the positioning mechanism 100 preferably comprises three or more positioning arm elements 100a configured to expand and contract about a fulcrum member 104 of the probe apparatus 70. Preferably, the positioning mechanism 100 (see FIG. 4) has three positioning arm elements 100a (see FIG. 4). However, the positioning mechanism 100 may have four positioning arm elements 100a, or another suitable number of positioning arm elements 100a. As further shown in FIG. 4, each positioning arm element 100a may be angled outwardly. As further shown in FIG. 4, each positioning arm element 100a has a first end 102a coupled to the aligning mechanism 98 and the foot portion 90. As further shown in FIG. 4, each positioning arm element 100a has a second end 102b coupled to a cone member 106 of the body portion 76 of the probe apparatus 70.

The cone member 106 (see FIG. 4) is preferably spring-loaded via an elastic element 108 (see FIG. 4), such as in the form of a spring 108a (see FIG. 4), and controls the tension of the positioning arm elements 100a (see FIG. 4). The tension and diameter adjustment of the positioning arm elements 100a (see FIG. 4) are preferably determined by the position of an adjusting element 110 (see FIG. 4), such as in the form of a knurled nut 110a (see FIG. 4), positioned on the shaft element 112 (see FIG. 4), such as in the form of a threaded central shaft element 112a (see FIG. 4). A threaded member 114 (see FIG. 4) for adjustable movement of the adjusting element 110 is preferably positioned on the shaft element 112 (see FIG. 4) adjacent the adjusting element 110 (see FIG. 4).

As shown in FIG. 4, the second end 74, such as in the form of sensor end 74a, further comprises the aligning mechanism 98 coupled to the positioning mechanism 100. The aligning mechanism 98 is configured to align the two or more eddy current elements 86 (see FIG. 4) in a perpendicular position with respect to cavity walls 115 (see FIG. 6B) of the annular cavity 28 (see FIG. 6B), such as in the form of tapered, annular cavity 28a (see FIG. 1B), when the probe apparatus 70 is positioned within the annular cavity 28. As further shown in FIG. 4, the aligning mechanism 98 preferably comprises three or more pivot joint mechanisms 98a each configured to rotate one of the three or more foot portions 90 to maintain alignment of the two or more eddy current elements 86 in the perpendicular position with respect to the cavity walls 115 (see FIG. 6B) of the annular cavity 28 (see FIG. 6B). Each pivot joint mechanism 98a (see FIG. 4) preferably comprises a pivot slot 97 (see FIG. 4) configured for movement of a pivot pin member 99 (see FIG. 4) within the pivot slot 97 in order to rotate or swivel the foot portion 90 on the pivot joint mechanism 98a (see FIG. 4), while the positioning arm element 100a (see FIG. 4) expands and contracts to accommodate for diameter changes.

Figure 5:
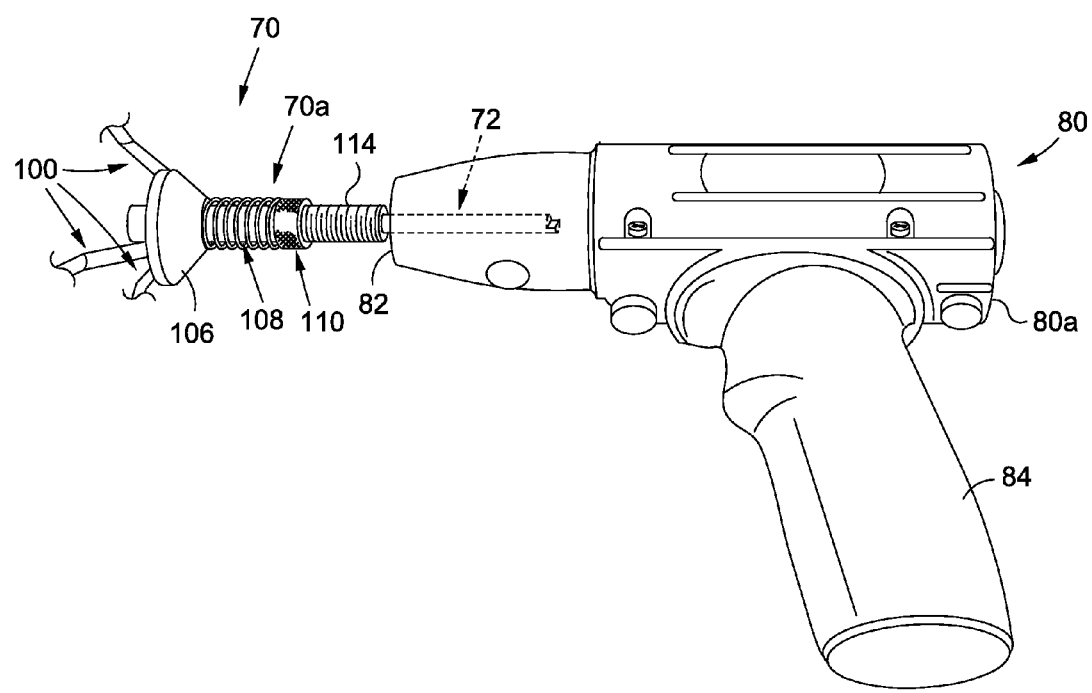
FIG. 5 is an illustration of a partial side perspective view of the probe apparatus of FIG. 4 attached to an embodiment of a rotating scanner device.

FIG. 5 is an illustration of a partial side perspective view of the probe apparatus 70, such as in the form of eddy current inspection probe apparatus 70a, of FIG. 4, attached to an embodiment of a rotating scanner device 80. Preferably, the rotating scanner device 80 (see FIGS. 5, 8) comprises a known eddy current inspection rotating scanner device 80a, such as, for example, a hand-held differential bridge eddy current inspection rotating scanner device, for emitting and receiving signals to and from the two or more eddy current elements 86 (see FIG. 4). As shown in FIG. 5, the rotating scanner device 80 has an attachment end 82 for receiving and attaching to the first end 72, such as in the form of connector end 72a (see FIG. 4), of the probe apparatus 70. As further shown in FIG. 5, the rotating scanner device 80 has a grip portion 84 so that an operator may manually grip or hold the rotating scanner 80 and attached probe apparatus 70 during inspection of the structure 24 (see FIG. 1A). Preferably, the probe apparatus 70 is designed to fit with and connect to known, commercial semi-automatic bolt-hole rotating scanner devices, such as obtained from Olympus Corporation of Tokyo, Japan, or obtained from UniWest of Pasco, Wash. However, other suitable rotating scanner devices, such as known eddy current inspection rotating scanner devices, may also be used. Preferably, such known rotating scanner devices 80 that may be used with the probe apparatus 70 disclosed herein have a frequency range of from about 100 Hz (Hertz) to about 6 MHz (Megahertz), and a speed range of from about 600 rpm (revolutions per minute) to about 3000 rpm.

Figure 6A:
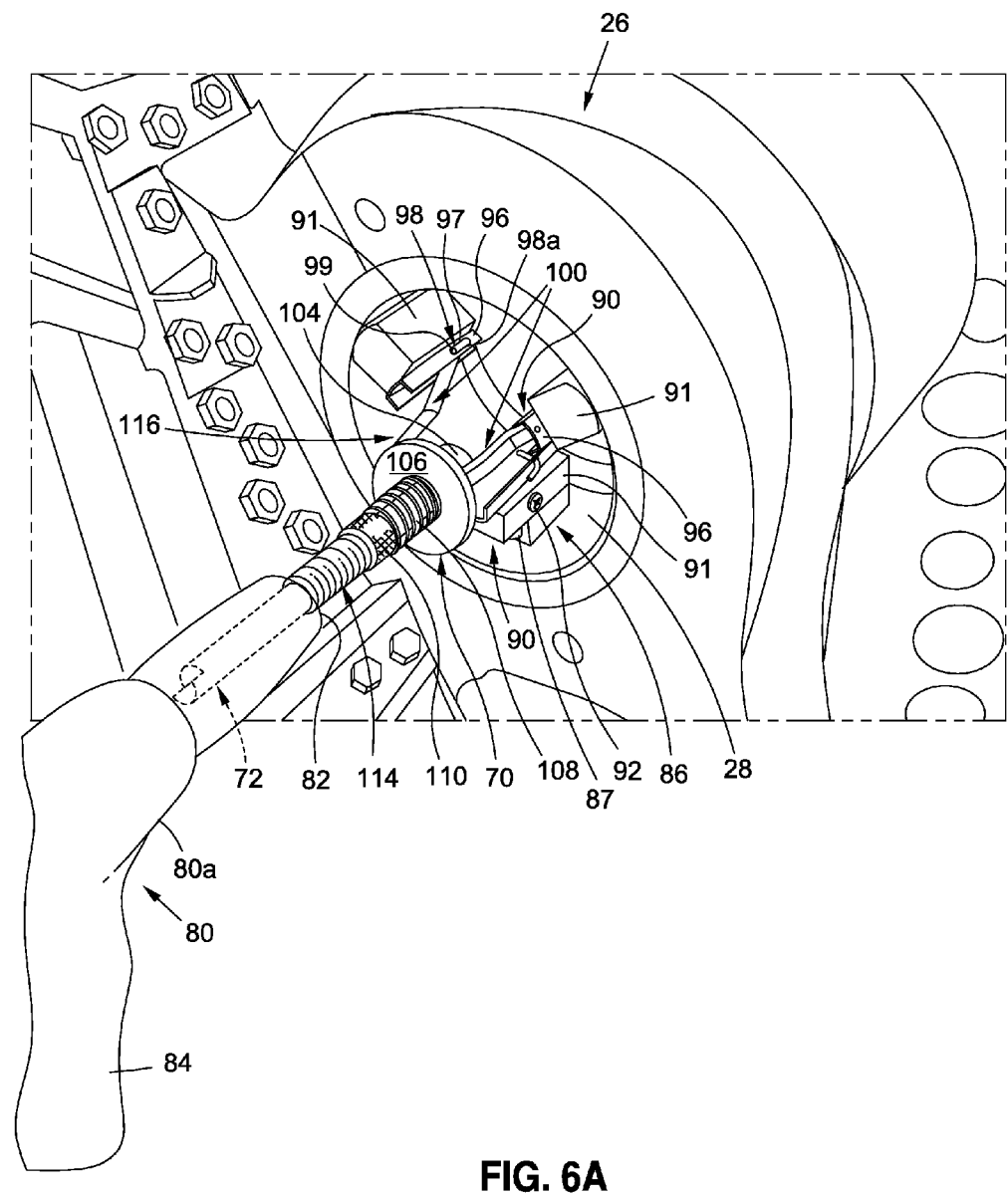
FIG. 6A is an illustration of a top perspective view of an embodiment of a probe apparatus attached to an embodiment of a rotating scanner device and inserted at a first position in an annular cavity of a structure to be inspected.
Figure 7:
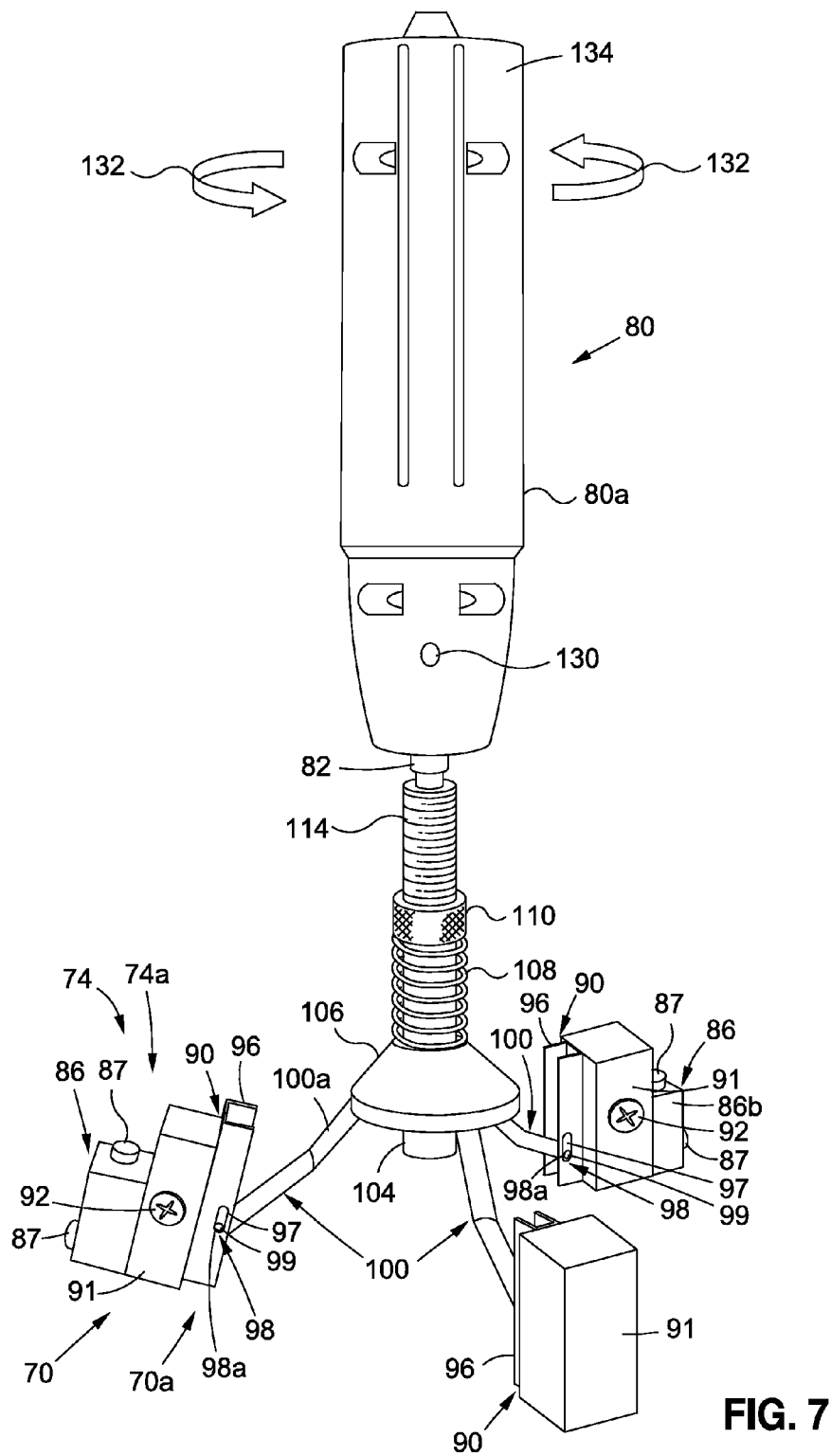
FIG. 7 is an illustration showing rotation of an embodiment of a rotating scanner device attached to an embodiment of a probe apparatus of the disclosure shown in a side perspective view.

FIG. 7 is an illustration showing rotation of an embodiment of the rotating scanner device 80 of FIG. 5 attached to an embodiment of the probe apparatus 70 of FIG. 4 shown in a side perspective view. FIG. 7 shows the rotating scanner device 80, such as in the form of eddy current inspection rotating scanner device 80a, (see also FIG. 5) which emits and receives signals to and from the two or more eddy current elements 86 (see FIG. 7). As shown in FIG. 7, the rotating scanner device 80 has attachment end 82 for attachment to the probe apparatus 70. As further shown in FIG. 7, the rotating scanner device 80 may have an LED (light-emitting diode) alarm indicator 130 and may further have an activation end 134. When the probe apparatus 70 (see FIG. 6A) is inserted into the annular cavity 28 (see FIG. 6A), the semi-automated rotating scanner device 80 may be activated to rotate the attached probe apparatus 70 in a rotational direction indicated by arrows 132 (see FIG. 7).

FIG. 8 is an illustration showing rotation of another embodiment of a rotating scanner device 80, such as in the form of eddy current inspection rotating scanner device 80b, attached to another embodiment of the probe apparatus 70, such as in the form of eddy current inspection probe apparatus 70b, shown in a side perspective view. As shown in FIG. 8, the rotating scanner device 80 comprises attachment end 82 and body portion 136. When the probe apparatus 70 (see FIG. 8) is inserted into the annular cavity 28 (see FIG. 1B), the semi-automated rotating scanner device 80 may be activated to rotate the attached probe apparatus 70 in a rotational direction indicated by arrows 138 (see FIG. 8). As further shown in FIG. 8, in this embodiment, the electromagnetic coil elements 87 of both the reference eddy current coil 86a (see FIG. 4) and the test eddy current coil 86b (see FIG. 4) are attached to one eddy current element 86, and the one eddy current element 86 is attached to one foot portion 90 of the three or more foot portions 90.

FIG. 6A is an illustration of a top perspective view of an embodiment of a probe apparatus 70 attached to an embodiment of a rotating scanner device 80, such as eddy current inspection rotating scanner device 80a, having an attachment end 82 attached to the first end 72 of the probe apparatus 70, and having grip portion 84 for handheld use by an operator. As shown in FIG. 6A, the probe apparatus 70 is inserted at a first position 116 in an annular cavity 28 of a structure 24 (see FIG. 1A), such as a terminal fitting 26 (see FIG. 6A), to be inspected.

Figure 6B:
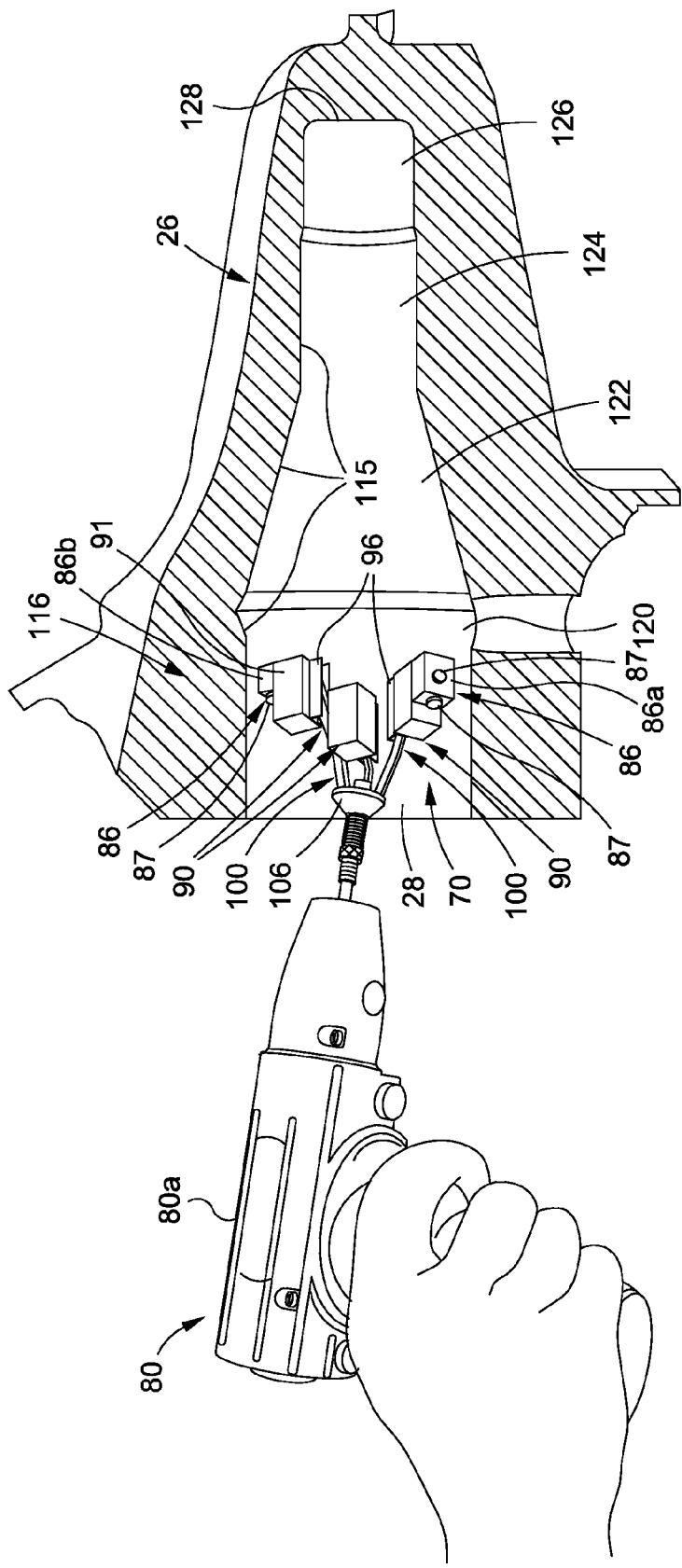
FIG. 6B is an illustration of a side perspective view of the probe apparatus and attached rotating scanner device of FIG. 6A inserted at a first position in an annular cavity shown in cross-section.
Figure 6C:
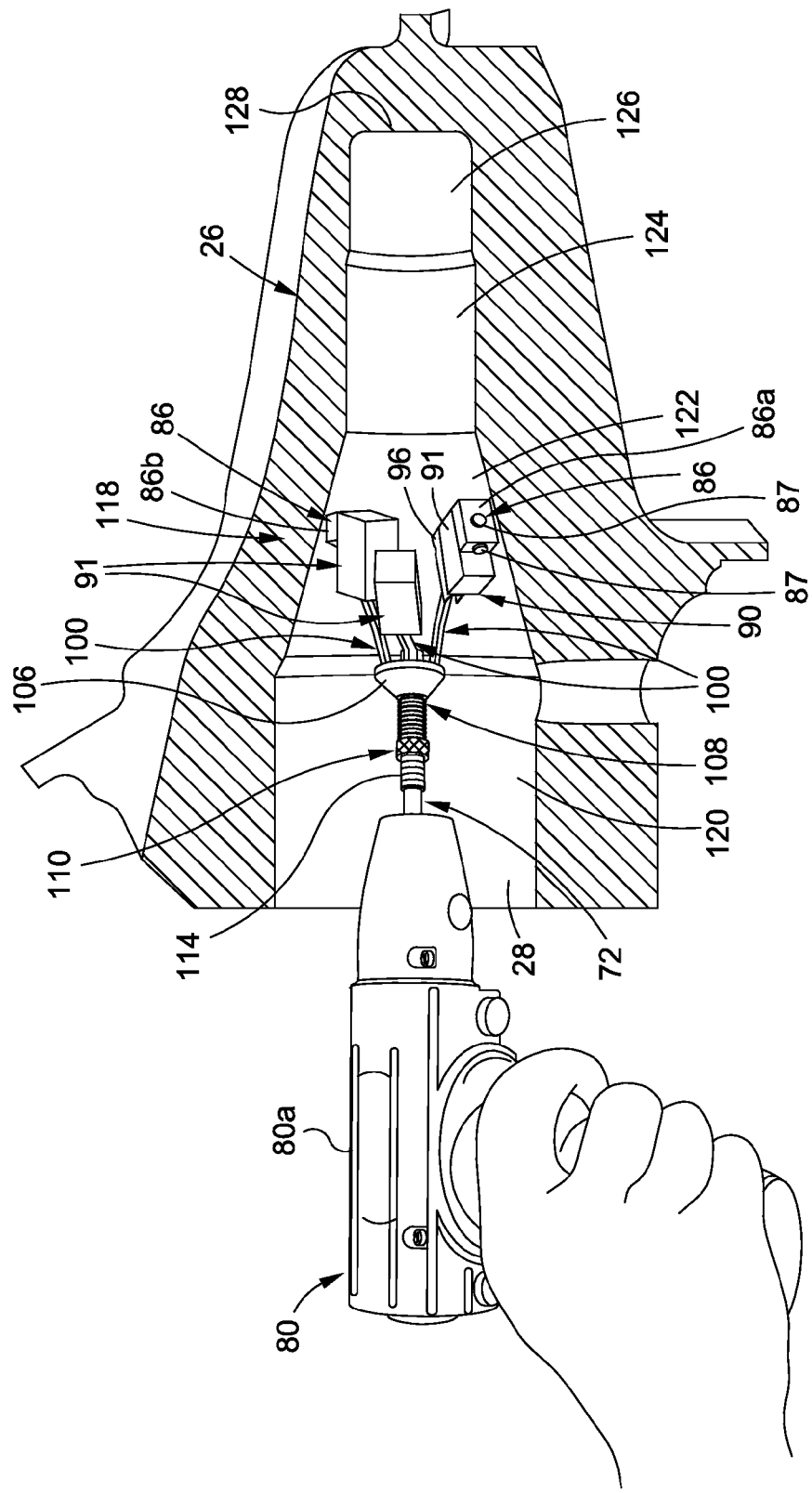
FIG. 6C is an illustration of a side perspective view of the probe apparatus and attached rotating scanner device of FIG. 6A inserted at a second position in an annular cavity shown in cross-section.

FIG. 6B is an illustration of a side perspective view of the probe apparatus 70 and attached rotating scanner device 80 of FIG. 6A inserted at the first position 116 in the annular cavity 28 which is shown in cross-section. FIG. 6C is an illustration of a side perspective view of the probe apparatus 70 and attached rotating scanner device 80 of FIG. 6A inserted at a second position 118 in the annular cavity 28 which is shown in cross-section.

As shown in FIG. 6A, the first end 72, such as in the form of connector end 72a (see FIG. 4) with connector plug 78 (see FIG. 4), connects or plugs into the rotating scanner device 80 and provides excitation and signal return to and from two eddy current elements 86 (see also FIG. 4) having the electromagnetic coil elements 87. As shown in FIG. 6A, each eddy current element 86 is mounted to the mounting element 91 of the foot portion 90 and each eddy current element 86 is attached to the mounting element 91 via attachment element 92. The probe apparatus 70 operates in a differential method where one eddy current element 86 is a reference eddy current coil 86a (see FIG. 6B) and the other eddy current element 86 is a test eddy current coil 86b (see FIG. 6B). This configuration allows for non-relevant geometry and surface conditions to be ignored. The eddy current elements 86 are preferably kept normal to the surface of the annular cavity 28, such as the tapered, annular cavity 28a (see FIG. 1B), due to the foot portions 90 (see FIGS. 6A-6C) rotating or swiveling on the pivot joint mechanism 98a (see FIG. 6A) while the positioning arm elements 100a of the positioning mechanism 100 (see FIGS. 6A-6C) expand and contract to accommodate for the diameter changes of the tapered, annular cavity 28a. The positioning arm elements 100a (see FIG. 4) of the positioning mechanism 100 (see FIG. 6A) expand and contract around the fulcrum member 104 (see FIG. 6A). The cone member 106 (see FIG. 6A), which is spring-loaded via elastic element 108 (see FIG. 6A), controls the tension of the positioning arm elements 100a. The tension and diameter adjustment are preferably determined by the position of the adjusting element 110 (see FIG. 6A) which may be adjustable on threaded member 114 (see FIG. 6A). Any crack or crack formation in the annular cavity 28 (see FIG. 6A) which is oriented perpendicular to the scanning direction of the eddy current element 86 (see FIGS. 6A-6C) may preferably be detected as an upward signal on the rotating scanner device 80 (see FIGS. 6A-6C).

Once the probe apparatus 70 is inserted into the bore, the semi-automated rotating scanner device 80 (see FIGS. 6A-6C) is activated to rotate and the probe apparatus 70 may be inserted into the annular cavity 28 (see FIG. 6A), such as the tapered, annular cavity 28a (see FIG. 1B), at the first position 116 (see FIGS. 6A-6B) in an entry and first bushing installation area 120 (see FIG. 6B). The probe apparatus 70 may then be inserted down the annular cavity 28 (see FIG. 6C), such as the tapered, annular cavity 28a (see FIG. 1B), at the second position 118 (see FIG. 6C) in a tapered inspection area 122 (see FIG. 6C), while an operator observes a measuring display instrument (not shown) either on the rotating scanner device 80 or attached separately to the rotating scanner device 80. Inspection time may be greatly reduced and due to the differential method being used, as well as the self-normalizing feature of the probe apparatus 70. As further shown in FIGS. 6B-6C, the annular cavity 28 of the terminal fitting 28 may further have a second bushing installation area 124 for a bushing 126 and an internal end 128 of the annular cavity 128. The probe apparatus 70 preferably performs the inspection in the tapered inspection area 122 (see FIG. 6C) and is preferably not inserted beyond the tapered inspection 122 into the second bushing installation area 124.

During eddy current testing and inspection of the annular cavity 28 of the structure 24 (see FIG. 1A), such as the terminal fitting 26 (see FIG. 6A), the probe apparatus 70 is preferably excited with an alternating current and induces an eddy current in the annular cavity 28, such as the tapered, annular cavity 28a (see FIG. 1B), of the terminal fitting 26 (see FIG. 6A) being inspected. Any discontinuities or material property variations that change the eddy current flow in the annular cavity 28, such as the tapered, annular cavity 28a (see FIG. 1B), of the terminal fitting 26 (see FIG. 6A) are preferably detected by the probe apparatus 70 as a potential defect, such as a crack or crack formation.

In another embodiment of the disclosure, there is provided a probe apparatus 70 for eddy current inspection of a tapered, annular cavity 28a (see FIG. 1B) of a structure 24 (see FIG. 1A) of an air vehicle 10 (see FIG. 1A), preferably where the tapered, annular cavity 28a (see FIG. 1B) has an outer diameter of greater than about two inches. The probe apparatus 70 (see FIG. 7) comprises a connector end 72a (see FIG. 4) configured to connect to a rotating scanner device 80 (see FIG. 7). The rotating scanner device 80 (see FIG. 7) preferably comprises an eddy current inspection rotating scanner device 80a (see FIG. 7) for emitting and receiving signals to and from a reference eddy current coil 86a (see FIG. 4) and a test eddy current coil 86b (see FIG. 4).

The probe apparatus 70 (see FIG. 7) further comprises a sensor end 74a (see FIG. 7) connected to the connector end 72a (see FIG. 4) via a body portion 76 (see FIG. 4). The sensor end 74a (see FIG. 7) comprises three foot portions 90 (see FIG. 7). The sensor end 74a (see FIG. 7) further comprises two eddy current elements 86 (see FIG. 7) comprising the reference eddy current coil 86a (see FIG. 4) attached to one foot portion 90 (see FIG. 7) and the test eddy current coil 86b (see FIG. 4) attached to another foot portion 90 (see FIG. 7). The sensor end 74 (see FIG. 7) further comprises the positioning mechanism 100 (see FIG. 7) configured to position the two or more eddy current elements 86 (see FIG. 7) against cavity walls 115 (see FIG. 6B) of a tapered, annular cavity 28a (see FIG. 1B) of a structure 24 (see FIG. 1A) of an air vehicle 10 (see FIG. 1A), such as an aircraft 11 (see FIG. 1A), to be inspected with the probe apparatus 70 (see FIG. 7), when the probe apparatus 70 is positioned within the tapered, annular cavity 28a (see FIG. 1B). The positioning mechanism 100 (see FIG. 7) preferably comprises three positioning arm elements 100a (see FIG. 7) configured to expand and contract about the fulcrum member 104 (see FIG. 7) of the probe apparatus 70 (see FIG. 7).

The sensor end 74 (see FIG. 7) further comprises the aligning mechanism 98 (see FIG. 7) coupled to the positioning mechanism 100 (see FIG. 7). The aligning mechanism 98 (see FIG. 7) is preferably configured to align the two or more eddy current elements 86 (see FIG. 7) in a perpendicular position with respect to the cavity walls 115 (see FIG. 6B) of the tapered, annular cavity 28a (see FIG. 1B), when the probe apparatus 70 (see FIG. 7) is positioned within the tapered, annular cavity 28. The aligning mechanism 98 (see FIG. 7) preferably comprises three pivot joint mechanisms 98a (see FIG. 7) each configured to rotate one of the three foot portions 90 (see FIG. 7) to maintain alignment of the two or more eddy current elements 86 (see FIG. 7) in the perpendicular position with respect to the cavity walls 115 (see FIG. 6B) of the tapered, annular cavity 28a (see FIG. 1B).

Figure 9:
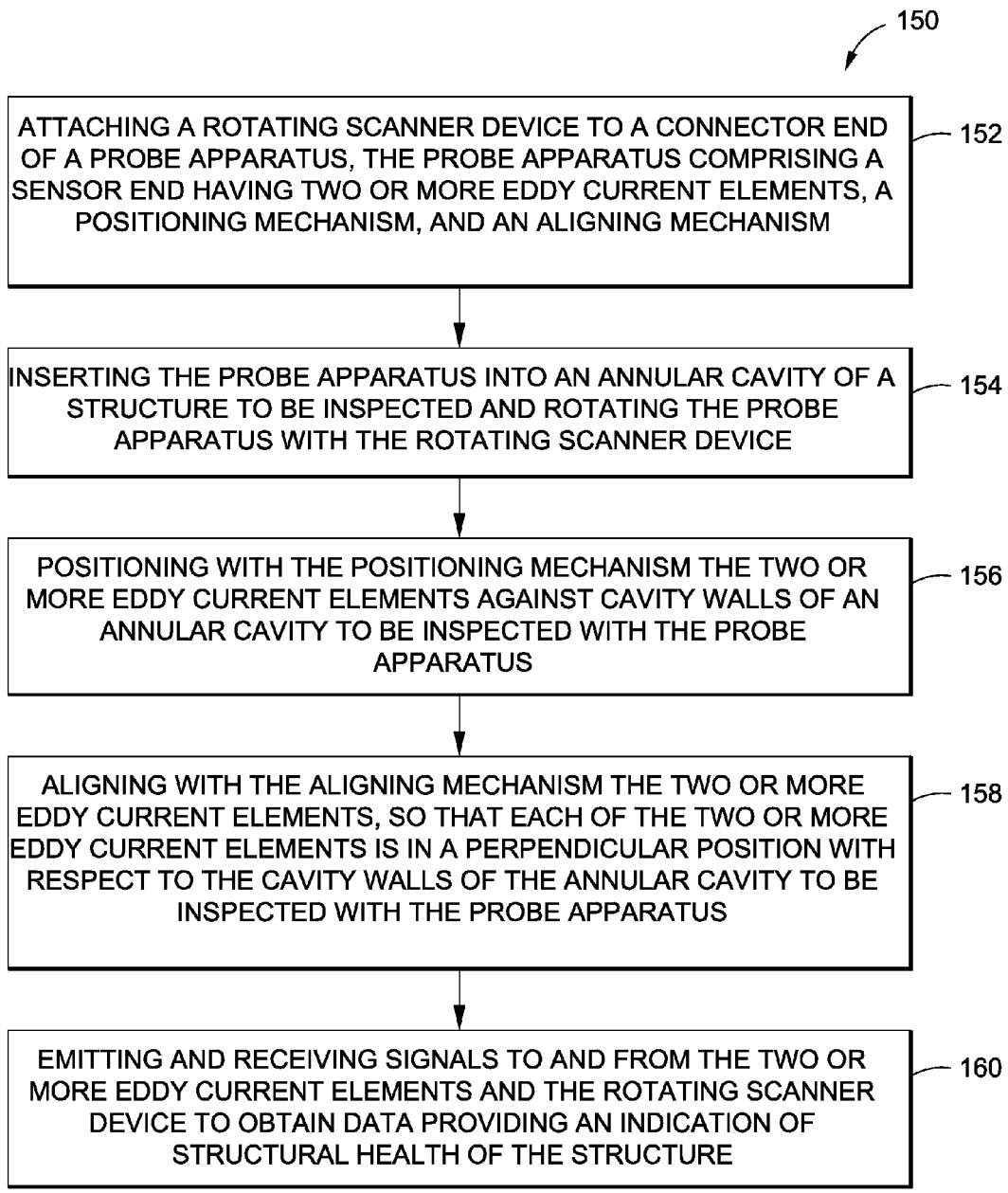

In another embodiment of the disclosure, there is provided a differential method 150 of performing an eddy current inspection of an annular cavity 28 (see FIG. 6A), such as a tapered annular cavity 28a (see FIG. 1B) of a structure 24 (see FIG. 1B), such as a terminal fitting 26 (see FIG. 6A). FIG. 9 is a flow diagram illustrating an embodiment of the method 150 of the disclosure. As shown in FIG. 9, the method 150 comprises step 152 of attaching a rotating scanner device 80 (see FIGS. 5, 8), such as in the form of an eddy current inspection rotating scanner device 80a, to a connector end 72a (see FIG. 4) of a probe apparatus 70 (see FIGS. 4-8). The probe apparatus 70 (see FIGS. 4-8) comprises a sensor end 74a (see FIG. 4) having two or more eddy current elements 86 (see FIG. 4), a positioning mechanism 100 (see FIG. 4), and an aligning mechanism 98 (see FIG. 4).

The attaching step 152 further comprises attaching an eddy current inspection rotating scanner device 80a (see FIG. 7) or 80b (see FIG. 8) to the connector end 72a (see FIG. 4). Preferably, the rotating scanner device 80 (see FIGS. 5, 8), such as in the form of the eddy current inspection rotating scanner device 80a, is a hand-held differential bridge eddy current inspection rotating scanner device. The attaching step 152 further comprises attaching a reference eddy current coil 86a (see FIG. 4) with electromagnetic coil elements 87 (see FIG. 4) to one foot portion 90 (see FIG. 4), and attaching a test eddy current coil 86b (see FIG. 4) with electromagnetic coil elements 87 (see FIG. 4) to another foot portion 90 (see FIG. 4). In another embodiment, the attaching step 152 further comprises attaching the electromagnetic coil elements 87 (see FIG. 8) of both the reference eddy current coil 86a and the test eddy current coil 86b to one eddy current element 86 (see FIG. 8) and attaching the one eddy current element (see FIG. 8) to one foot portion 90 (see FIG. 8).

As further shown in FIG. 9, the method 150 comprises step 154 of inserting the probe apparatus into an annular cavity 28 (see FIG. 6A), such as the tapered annular cavity 28a (see FIG. 1B) of the structure 24 (see FIG. 1B), such as the terminal fitting 26 (see FIG. 6A), to be inspected and rotating the probe apparatus 70 (see FIGS. 4-8) with the rotating scanner device (see FIGS. 5, 8). The inserting step 154 further comprises inserting the probe apparatus 70 (see FIGS. 4-8) into a tapered annular cavity 28a (see FIG. 1B) of the structure 24 (see FIG. 1B), such as a terminal fitting 26 (see FIG. 6A), where the tapered annular cavity 28a (see FIG. 1B) preferably has an outer diameter of greater than about two inches, and more preferably has an outer diameter of greater than about two inches and less than about six inches.

As further shown in FIG. 9, the method 150 comprises step 156 of positioning with the positioning mechanism 100 (see FIG. 4) the two or more eddy current elements 86 (see FIG. 4) against cavity walls 115 (see FIG. 6B) of the annular cavity 28 (see FIG. 6A) to be inspected with the probe apparatus 70 (see FIGS. 4-8). The positioning step 156 further comprises positioning the two or more eddy current elements 86 (see FIG. 4) with three or more positioning arm elements 100a (see FIG. 4), each positioning arm element 100a configured to expand and contract about a fulcrum member 104 (see FIG. 4) of the probe apparatus 70 (see FIGS. 4-8).

As further shown in FIG. 9, the method 150 comprises step 158 of aligning with the aligning mechanism 98 (see FIG. 4) the two or more eddy current elements 86 (see FIG. 4), so that each of the two or more eddy current elements 86 (see FIG. 4) is in a perpendicular position with respect to the cavity walls 115 (see FIG. 6B) of the annular cavity 28 (see FIG. 6B) to be inspected with the probe apparatus 70 (see FIGS. 4-8). The aligning step 158 further comprises aligning with three or more pivot joint mechanisms 98a (see FIG. 4), each pivot joint mechanism 98a configured to rotate one foot portion 90 (see FIG. 4) of the three or more foot portions 90 (see FIG. 4), each foot portion 90 being coupled to the aligning mechanism 98, to maintain alignment of the two or more eddy current elements 86 (see FIG. 4) in the perpendicular position with respect to the cavity walls 115 (see FIG. 6B) of the annular cavity 28 (see FIG. 6B).

As further shown in FIG. 9, the method 150 comprises step 160 of emitting and receiving signals to and from the two or more eddy current elements 86 (see FIG. 4) and the rotating scanner device 80 (see FIGS. 7, 8) to obtain data providing an indication of structural health of the structure 24 (see FIG. 1B), such as a terminal fitting 26 (see FIG. 6A). The emitting and receiving signals step 160 further comprises detecting as an upward signal on the rotating scanner device 80 (see FIGS. 7, 8) any crack or crack formation in the annular cavity 28 (see FIG. 6B) oriented perpendicular to a scanning direction of the two or more eddy current elements 86 (see FIG. 4).

Disclosed embodiments of the probe apparatus 70 (see FIGS. 4-8) and method 150 (see FIG. 9) allow for improved non-destructive inspection (NDI) of inspection areas that may be difficult to access and that may be difficult to visually observe the inspection procedure and results. This may result in improved detection of cracks and crack formations in critical areas, such as terminal fittings 26 (see FIG. 1B), that attach the wings 18 (see FIG. 1A) to an aircraft 11 (see FIG. 1A). In addition, disclosed embodiments of the probe apparatus 70 (see FIGS. 4-8) and method 150 (see FIG. 9) allow for performing eddy current surface probe crack and crack formation non-destructive inspections in difficult to access, large diameter, non-cylindrical, annular cavities 28 (see FIG. 1B), such as tapered, annular cavities 28a (see FIG. 1B), in structures 24 (see FIG. 1A) of aircraft 11 (see FIG. 1A), such as terminal fittings 26 (see FIG. 1B) and the like. This may result in decreased labor, time, and costs to conduct such inspections. Moreover, inspection time may be greatly reduced, as compared to inspections using existing NDI devices and methods, due to the self-normalizing feature of the probe apparatus 70 (see FIGS. 4-8), and due to operation of the probe apparatus 70 (see FIGS. 4-8) using a differential method, where one eddy current element 86 (see FIG. 4) is a reference eddy current coil 86a (see FIG. 4) and another eddy current element 86 (see FIG. 4) is a test eddy current coil 86b (see FIG. 4).

Further, disclosed embodiments of the probe apparatus 70 (see FIGS. 4-8) and method 150 (see FIG. 9) allow for the probe apparatus 70 (see FIGS. 4-8) to be attached to existing commercial rotating scanner devices 80 (see FIGS. 7, 8), such as eddy current inspection rotating scanner devices 80a (see FIG. 7) and 80b (see FIG. 8), for example, a hand-held differential bridge eddy current inspection rotating scanner device, and inserted into the tapered, annular cavity 28a (see FIG. 1B) or bore. In addition, the configuration of the probe apparatus 70 (see FIGS. 4-8) allows the eddy current elements 86 (see FIG. 4) to stay in contact and normal to the surface throughout inspection of the tapered inspection area 122 (see FIG. 6B). Moreover, the method 150 (see FIG. 9) allows for semi-automated inspection of the tapered annular cavity 28a (see FIG. 1B) or bore with the only access needed being for the probe apparatus 70 (see FIGS. 4-8) and an operator's hand.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive.

Although specific terms are employed herein, they are used in a generic and descriptive sense only and not for purposes of limitation.

What is claimed is:

1. A probe apparatus comprising:
    a first end configured to connect to a rotating scanner device; and,
    a second end comprising:
        two or more eddy current elements comprising at least one reference eddy current coil and at least one test eddy current coil;
        a positioning mechanism configured to position the two or more eddy current elements against cavity walls of an annular cavity of a structure to be inspected with the probe apparatus, when the probe apparatus is positioned within the annular cavity;
        an aligning mechanism coupled to the positioning mechanism, the aligning mechanism configured to align the two or more eddy current elements in a perpendicular position with respect to the cavity walls of the annular cavity, when the probe apparatus is positioned within the annular cavity; and
        three or more foot portions, each foot portion attached to the positioning mechanism and attached to the aligning mechanism, and each foot portion comprising a mounting element and a base element, the mounting element having a first side attached to one eddy current element and having a second side attached to the base element.

2. The apparatus of claim 1 wherein the first end comprises a connector end having a connector plug configured to connect to the rotating scanner device, and wherein the second end comprises a sensor end.

3. The apparatus of claim 1 wherein electromagnetic coil elements of the two or more eddy current elements are coupled to at least one of the three or more foot portions.

4. The apparatus of claim 3 wherein the aligning mechanism comprises three or more pivot joint mechanisms each configured to rotate one of the three or more foot portions to maintain alignment of the two or more eddy current elements in the perpendicular position with respect to the cavity walls of the annular cavity.

5. The apparatus of claim 1 wherein the second end comprises two eddy current elements comprising the reference eddy current coil and the test eddy current coil.

6. The apparatus of claim 5 wherein the reference eddy current coil is attached to one of the three or more foot portions, and the test eddy current coil is attached to another one of the three or more foot portions.

7. The apparatus of claim 5 wherein the electromagnetic coil elements of both the reference eddy current coil and the test eddy current coil are attached to one eddy current element and the one eddy current element is attached to one of the three or more foot portions.

8. The apparatus of claim 1 wherein the positioning mechanism comprises three or more positioning arm elements configured to expand and contract about a fulcrum member of the probe apparatus, each positioning arm element angled outwardly from the fulcrum member before, during and after inspection of the structure to be inspected with the probe apparatus.

9. The apparatus of claim 1 wherein the rotating scanner device comprises an eddy current inspection rotating scanner device for emitting and receiving signals to and from the two or more eddy current elements.

10. The apparatus of claim 1 wherein the annular cavity of the structure to be inspected is tapered, and further wherein the annular cavity has an outer diameter of greater than about two inches.

11. A probe apparatus for eddy current inspection of a tapered, annular cavity of a structure of an air vehicle, the probe apparatus comprising:
    a connector end configured to connect to a rotating scanner device; and,
    a sensor end connected to the connector end via a body portion, the sensor end comprising:
        three foot portions, each foot portion comprising a mounting element attached to a base element;
        two eddy current elements comprising a reference eddy current coil attached to the mounting element of one foot portion and a test eddy current coil attached to the mounting element of another foot portion;
        a positioning mechanism comprising three positioning arm elements, each positioning arm element attached to each respective foot portion, the positioning mechanism configured to position the two eddy current elements against cavity walls of the tapered, annular cavity of the structure of the air vehicle to be inspected with the probe apparatus, when the probe apparatus is positioned within the tapered, annular cavity; and,
        an aligning mechanism comprising three pivot joint mechanisms, each pivot joint mechanism attached to each respective foot portion, the aligning mechanism coupled to the positioning mechanism, the aligning mechanism configured to align the two eddy current elements in a perpendicular position with respect to the cavity walls of the tapered, annular cavity, when the probe apparatus is positioned within the tapered, annular cavity.

12. The apparatus of claim 11 wherein the three positioning arm elements are configured to expand and contract about a fulcrum member of the probe apparatus, each positioning arm element angled outwardly from the fulcrum member before, during and after inspection of the air vehicle to be inspected with the probe apparatus.

13. The apparatus of claim 11 wherein the three pivot joint mechanisms are each configured to rotate one of the three foot portions to maintain alignment of the two eddy current elements in the perpendicular position with respect to the cavity walls of the tapered, annular cavity.

14. The apparatus of claim 11 wherein the rotating scanner device comprises an eddy current inspection rotating scanner device for emitting and receiving signals to and from the reference eddy current coil and the test eddy current coil.

15. A differential method of performing an eddy current inspection of an annular cavity of a structure, the method comprising the steps of:
    attaching a rotating scanner device to a connector end of a probe apparatus, the probe apparatus comprising a sensor end comprising:
        two or more eddy current elements comprising at least one reference eddy current coil and at least one test eddy current coil;
        a positioning mechanism;
        an aligning mechanism coupled to the positioning mechanism; and
        three or more foot portions, each foot portion attached to the positioning mechanism and attached to the aligning mechanism, and each foot portion comprising a mounting element and a base element, the mounting element having a first side attached to one eddy current element and having a second side attached to the base element:

inserting the probe apparatus into the annular cavity of the structure to be inspected and rotating the probe apparatus with the rotating scanner device;

positioning with the positioning mechanism the two or more eddy current elements against cavity walls of the annular cavity to be inspected with the probe apparatus;

aligning with the aligning mechanism the two or more eddy current elements, so that each of the two or more eddy current elements is in a perpendicular position with respect to the cavity walls of the annular cavity to be inspected with the probe apparatus; and, emitting and receiving signals to and from the two or more eddy current elements and the rotating scanner device to obtain data providing an indication of structural health of the structure.

16. The method of claim 15 wherein the step of attaching the rotating scanner device to the connector end of the probe apparatus further comprises attaching the reference eddy current coil having electromagnetic coil elements to one foot portion and attaching the test eddy current coil having electromagnetic coil elements to another foot portion.

17. The method of claim 15 wherein the step of attaching the rotating scanner device to the connector end of the probe apparatus further comprises attaching electromagnetic coil elements of both the reference eddy current coil and the test eddy current coil to one eddy current element and attaching the one eddy current element to one foot portion.

18. The method of claim 15 wherein the step of inserting the probe apparatus into the annular cavity of the structure further comprises inserting the probe apparatus into a tapered, annular cavity of the structure, the tapered, annular cavity having an outer diameter of greater than about two inches.

19. The method of claim 15 wherein the step of positioning with the positioning mechanism further comprises positioning the two or more eddy current elements with three or more positioning arm elements, each positioning arm element configured to expand and contract about a fulcrum member of the probe apparatus, and each positioning arm element angled outwardly from the fulcrum member before, during and after performance of the eddy current inspection.

20. The method of claim 15 wherein the step of aligning with the aligning mechanism further comprises aligning with three or more pivot joint mechanisms each configured to rotate a foot portion coupled to the aligning mechanism to maintain alignment of the two or more eddy current elements in the perpendicular position with respect to the cavity walls of the annular cavity.

* * * * *